United States Patent [19]

Suzuki

[11] Patent Number: 5,472,433

[45] Date of Patent: * Dec. 5, 1995

[54] DISPOSABLE SAFETY GUARD FOR SYRINGE NEEDLES AND THE LIKE

[76] Inventor: George R. Suzuki, 12861 Wheeler Pl., Santa Ana, Calif. 92705

[*] Notice: The portion of the term of this patent subsequent to Nov. 29, 2011, has been disclaimed.

[21] Appl. No.: 143,337

[22] Filed: Oct. 26, 1993

Related U.S. Application Data

[63] Continuation-in-part of Ser. No. 994,978, Dec. 22, 1992, Pat. No. 5,368,580.

[51] Int. Cl.$^6$ ........................................ A61M 5/00
[52] U.S. Cl. ..................... 604/263; 604/192; 206/265; 206/266
[58] Field of Search ................................. 604/263, 192, 604/110; 128/919; 206/363–367, 370; 29/240; 439/863, 400, 417, 410, 411; 221/279; 312/71

[56] References Cited

U.S. PATENT DOCUMENTS

| | | | |
|---|---|---|---|
| 2,769,154 | 10/1956 | Greenbaum | 439/410 |
| 4,846,803 | 7/1989 | Emerson | 604/263 |
| 4,917,243 | 4/1990 | Abrams et al. | 206/365 |
| 4,929,241 | 5/1990 | Kulli | 604/263 |
| 5,017,189 | 5/1991 | Boumendil | 604/192 |
| 5,046,612 | 9/1991 | Mostarda et al. | 206/365 |
| 5,084,028 | 1/1992 | Kennedy et al. | 604/192 |
| 5,188,612 | 2/1993 | Herrington, Jr. et al. | 604/192 |
| 5,230,426 | 7/1993 | Keefe et al. | 206/205 |
| 5,275,280 | 1/1994 | Everhart | 206/366 |
| 5,334,151 | 8/1994 | Santilli | 604/192 |

Primary Examiner—C. Fred Rosenbaum
Assistant Examiner—V. Alexander
Attorney, Agent, or Firm—Leonard Tachner

[57] ABSTRACT

A disposable safety guard for syringe needles and the like, the safety guard being adapted to laterally receive the tip of a needle in an elongated interior chamber within a body member. The interior encloses a high frictional surfaced gripping device which receives the syringe needle in a lateral direction and prevents the needle from being removed therefrom, after it is secured therein. In a preferred embodiment, the gripping mechanism comprises a rectangular shaped plastic component having two planar members joined by a thinned or living hinge permitting the component to be folded in half so that it may conform to the shape of the interior of the body member and close upon the needle. In that preferred embodiment of the invention, a series of ridges on the folded interior surface of the gripper component increases the frictional engagement with the syringe needle. The gripper component has a pair of lips designed to engage a plurality of ratchet teeth in the interior walls of the body member chamber. The lips prevent the gripper from moving in a vertically upward direction within the interior and thus cooperate with the ratchet teeth in the interior of the body member to form a one way ratcheting effect. The ralationship between the lips and the ratchet teeth creates a leverage effect much like a nut cracker to firmly grasp and retain a needle of virtually any standard size.

4 Claims, 5 Drawing Sheets

FIG. 3a
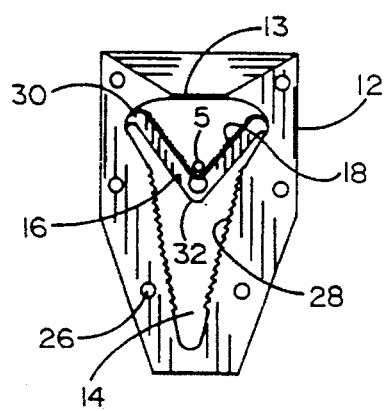
FIG. 3b
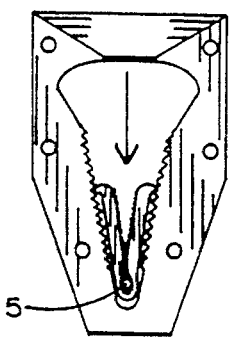
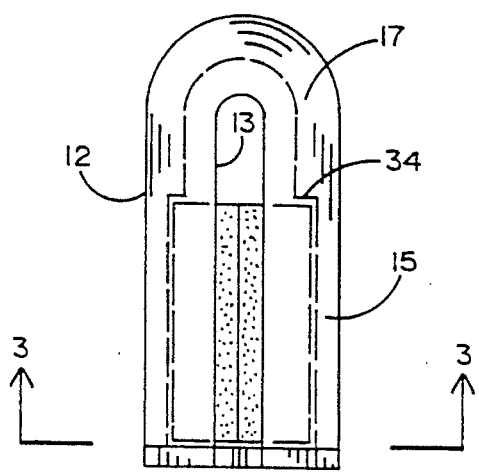
FIG. 4
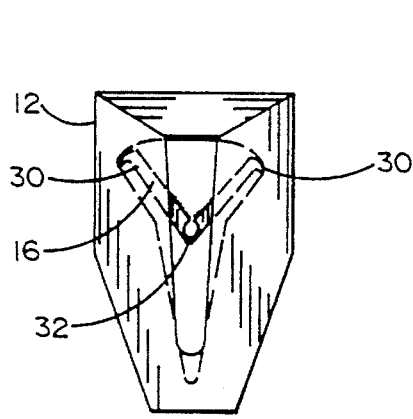
FIG. 5
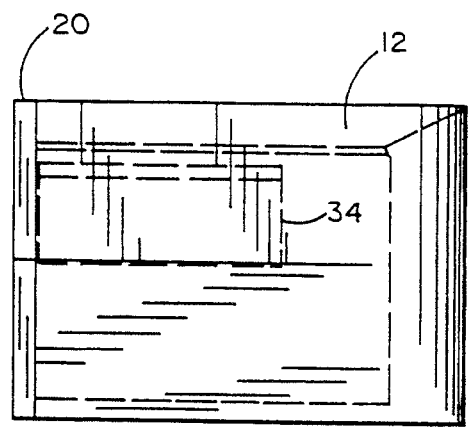
FIG. 6

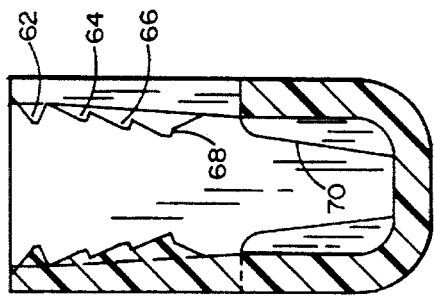
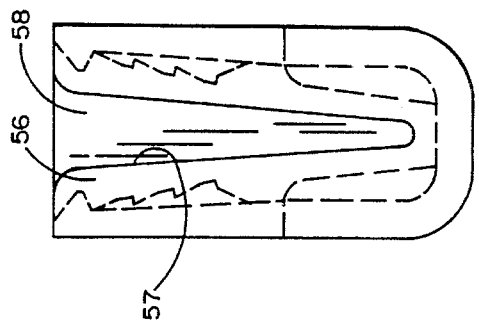
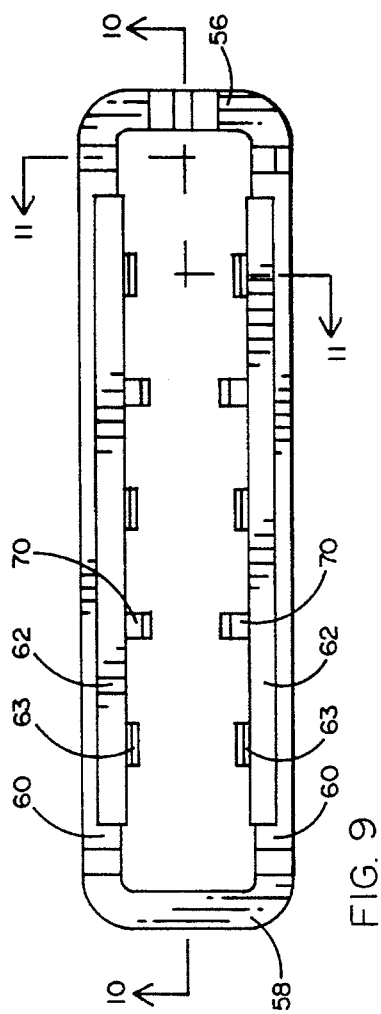
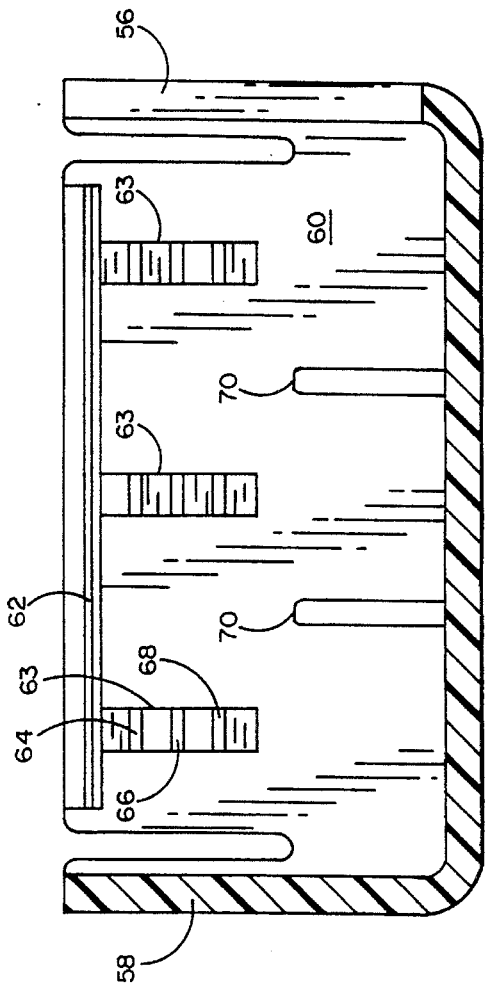

5,472,433

DISPOSABLE SAFETY GUARD FOR SYRINGE NEEDLES AND THE LIKE

CROSS-REFERENCE TO RELATED APPLICATION

The present application is a continuation-in-part of Application Ser. No. 07/994,978 filed on Dec. 22, 1992, now U.S. Pat. No. 5,368,580.

BACKGROUND OF THE INVENTION

1. Field of the Invention

The present invention relates generally to the field of protective devices used in the disposal of hypodermic needles for protection against the inadvertent spread of disease therefrom and more specifically to a safety guard for use in disposing used syringe needles, the guard being adapted to receive and entirely enclose the pointed end of the needle to prevent inadvertent pricking of the hands or other body parts and cause the inadvertent spread of contagious disease carried in blood or other bodily liquids contained within the used needle.

2. Prior Art

Concern over the inadvertent spread of blood carried contagious disease such as HIV and HBV virus, has significantly altered the method in which various medical services are administered in hospitals, doctors' offices, dentists' offices and the like. One such area of concern is the use and disposal of syringe needles and the like because of the extremely high risk of inadvertent pricking of the hands or other body parts with a needle that has already been exposed to blood or other bodily fluids containing a contagious disease. Consequently, the prior art includes issued U.S. Patents which disclose a variety of different means for averting such inadvertent pricking of the hands or other body parts by a used needle. Each such prior art patent discloses at least one device for protectively covering the needle after its use and prior to its disposal so that neither the administering medical personnel, such as a physician or nurse, nor any personnel handling disposed needles, can inadvertently come in contact with the pointed end of the needle. Such contact could, of course, pierce the skin and pass the contagious blood or other liquid to such personnel. In this regard, a novelty search conducted by the inventor herein has turned up the following U.S. Patents which are deemed to be relevant to the present invention to varying degrees.

U.S. Pat. No. 5,046,612 to Mostarda et al is directed to a safety apparatus for extracting hypodermic needles from a syringe. The apparatus comprises a rigid receptacle 1 having a horizontally arranged longitudinal configuration, V-shaped notches 2 and 2' respectively provided in the upper borders of the front and rear ends, rigid flaps 3 and 3' integrally linked in the notches 2 and 2', a longitudinal slot 4 disposed at the converging zone of the rigid flaps 3 and 3' and having an enlargement 7, projections 10 provided in the facing borders of the enlargement 7 for preventing the release of the rear end of a hypodermic needle 5 extracted from its seat in a syringe nozzle, and a slot 9 projecting downward from the apex of notch 2. Slot 4 is adapted to receive hypodermic needles and is provided with an enlargement 7 adapted to permit the passage of an enlarged rear end or cone 8 of a hypodermic needle, and a plurality of projections 12 and 12' provided on both borders of the slot 4 in the manner of teeth mutually overlaid U.S. Pat. No. 4,917,243 to Abrams et al is directed to a needle disposal device. The disposal device 1 comprises a container portion having an elongated slit 3 located near the upper surface of the container portion extending along the length of the container portion in an axial direction, a retainer means including a pair of opposing flaps 4 extending a distance into the slit 3, and a U-shaped opening 5 located in one end of the container that receives the neck of a syringe for separating a needle from the syringe neck.

U.S. Pat. No. 4,643,722 to Smith, Jr. is directed to a hypodermic needle closure system. The system includes an elongated closure 20 having an elongated slot 30 formed therein, an axial bore 44 communicating with slot 30, a closed upper end 40 and an open lower end 42, a radial enlargement 36 adjacent the lower end 42, and a portion 38 underlying enlargement 36 and having a cylindrical configuration to facilitate engagement of the closure 20 with a needle hub for retention purposes. As shown in FIG. 9, the slot 30 permits lateral insertion of a needle 4 into the closure 20.

U.S. Pat. No. 5,084,028 to Kennedy et al is directed to a needle covering dispenser. The device comprises a dispenser 10 having an internal cavity 12 adapted to store a plurality of needle covers 14. Each needle cover 14 has an internal cavity 24 that accommodates a needle, an entrance aperture 22 through the internal cavity 24 having upper and lower inwardly angled teeth 28 which grip the base of the needle and secure the needle within the needle cover 14, and wedge-shaped slits 26 on the opposite sides which accommodate needle wings 31.

U.S. Pat. No. 4,848,569 to Leishman is directed to an apparatus for disposing of contaminated needles. The apparatus 10 comprises an elongated housing 30 defining a passage 31 having upper and lower openings 32 and 33, respectively, and an elongated outwardly opened channel 34 extending along the passage 31 between openings 32 and 33; and a plurality of shields 12 disposed in passage 31. Shields 12 are retained in passage 31 by strips of adhesive 41 and 42, respectively, removably disposed over the upper and lower openings 32 and 33. Shields 12 are made from a suitable material that can be penetrated by the tip of a hypodermic needle. When the device 11 is ready for use, the user simply removes the strip of adhesive 41 disposed over the upper opening 32.

Although many of the aforementioned disclosed prior art attempts at solving the problem addressed herein are functionally capable of achieving the protective result intended by the present inventor, they unfortunately suffer from one or more significant disadvantages which tend to reduce the likelihood of use in an actual hospital environment or physicians or dentists office. By way of example, any of the aforementioned prior art disclosures which require structural alteration to the syringe itself, would be disadvantageous because of the additional expense involved in making such modifications to the syringe. Furthermore, any such prior art which is designed to operate with syringe needles of a certain diameter or a certain length are disadvantageous because they must be available in a variety of different sizes in order to accommodate different size syringe needles. Even those prior art devices that don't require alteration of the syringe structure and which can accommodate all sizes of syringe needles can be disadvantageous if they are costly because of complex shapes, structures or materials because such devices will be used only once and then disposed along with the syringe. Any such device which significantly increases the cost of using a syringe and disposing of a syringe is unlikely to find its way into actual use or is likely to increase the cost of healthcare which is already under significant rising pressure. Thus, there is a continuing need for a disposable safety device for use on syringe needles which does not present any one or more of the aforementioned disadvantages of the prior art. More specifically, there is a need for such a safety device which does not require modification of the syringe structure, which does not depend upon the length or diameter of the needle or the size or shape of any other portion of the syringe and which is of relatively simple and low cost design so that it does not significantly increase the cost of administering healthcare and is thus more likely to be used by hospitals, physicians, dentists and the like.

SUMMARY OF THE INVENTION

The present invention solves the aforementioned long felt need by providing a disposable safety guard for syringe needles and the like, the safety guard being adapted in a first embodiment to receive the tip of a needle in a wedge or V-shaped interior chamber within a body member. The interior encloses a high frictional surfaced gripping device which receives the syringe needle in a lateral direction and prevents the needle from being removed therefrom, after it is secured therein in a manner to be described hereinafter in more detail. In a preferred embodiment of the invention disclosed herein, the gripping mechanism within the interior of the body member comprises a rectangular shaped plastic component having two planar members joined by a thinned or living hinge permitting the component to be folded in half so that it may conform to the shape of the interior of the body member and close upon the needle. In that preferred embodiment of the invention, a layer of coarse grain sandpaper is placed on the folded interior surface of the gripper component in order to increase the frictional engagement with the syringe needle. The gripper component has a pair of lips designed to engage a plurality of horizontally disposed grooves in the interior walls of the body member chamber so that as the gripper and sandpaper are pushed toward to bottom or apex of the V-shaped interior of the body member by the syringe needle, the lips prevent the gripper from moving in a vertically upward direction within the interior and thus cooperate with the grooves in the interior of the body member to form a one way ratcheting effect. The gripper and sandpaper combination is also prevented from moving horizontally in one direction by a shoulder within the interior wall surfaces of the body member and in the other direction by a face member which is secured to the body member and which provides an elongated opening, sufficiently large to receive the syringe needle, but sufficiently narrow to prevent the gripper and sandpaper from moving in the direction of the face member. Except for the sandpaper used in the preferred embodiment herein, all of the elements of the present invention may be made of relatively inexpensive plastic such as styrene that may be injection molded. In a preferred embodiment of the invention herein, a plurality of safety guards are contained within a dispenser which serves the dual purpose of conveniently housing a large number of such guards and also permitting the user to grasp the dispenser instead of the guard to further reduce the risk of inadvertent pricking of the hands or other body parts while the needle is inserted into the guard for disposal therewith.

A second embodiment of the invention disclosed herein employs a two-piece design which is especially advantageous for low-cost injection molded fabrication with simple and expedient assembly. Unlike the first embodiment, the second embodiment employs an interior chamber which is uniform in cross-section from top to bottom with vertical, parallel walls. However, three opposing pairs of ratchet teeth having increasing thickness from top to bottom of the chamber, provide the wedge-closing effect of the V-shaped interior of the first embodiment. An elongated flange integral to the upper edge of the chamber walls prevents the gripper from rising above the top of the chamber. The gripper has a pair of top lips to engage the flange and the ratchet teeth. The gripper also has a plurality of elongated horizontal interior ridges which are adapted to engage the syringe needle. The interior surface of the gripper may also be seeded with sandpaper-like particles to further increase needle-gripping-friction. The resulting needle guard is low in cost, simple to manufacture and assemble and conducive to one-hand, easy operation. Furthermore, a leverage effect resulting from the compression of the lips by the ratchet teeth, assures a firm, secure grasp of the needle much like a nut cracker would compress the shell of a nut.

OBJECTS OF THE INVENTION

It is therefore a principal object of the present invention to provide a disposable safety guard for use with syringe needles and the like to prevent inadvertent pricking of the hands or other body parts by a used needle which might otherwise transfer a contagious disease from the blood or other liquid contained in the needle, the guard of the present invention being independent of needle size and obviating any requirement for structural alterations to the syringe or needle.

It is an additional object of the present invention to provide a disposal safety guard for syringe needles, wherein the guard is made of a relatively inexpensive plastic material that may be injection molded in mass quantities to reduce the cost thereof.

It is still an additional object of the present invention to provide a disposal safety guard for use with syringe needles and the like by using a minimum number of parts that are made of inexpensive plastic and further using a design which enables lateral insertion of the needle tip into the invention for disposal therewith.

It is still a further object of the present invention to provide a safety system comprising a plurality of disposable safety guards for use with used syringe needles, the safety guards being provided in a dispenser which serves the dual purpose of conveniently housing a plurality of such guards and also providing a method for further distancing the user's hands and the syringe needle during insertion of the needle in the guard using only one hand to reduce the risk of inadvertent pricking therewith.

BRIEF DESCRIPTION OF THE DRAWINGS

The aforementioned objects and advantages of the present invention, as well as additional objects and advantages thereof will be more fully understood hereinafter as a result of a detailed description of a preferred embodiment when taken in conjunction with the following drawings in which:

FIG. 3 comprising FIGS. 3A and 3B is an end view of the main body of the first embodiment with the cover removed therefrom showing, respectively, the uppermost and lowermost positions of a gripper component;

FIG. 4 is a top view of the assembled configuration of the first embodiment;

FIG. 5 is a front view of the assembled configuration of the first embodiment;

FIG. 6 is a side view of the assembled configuration of the first embodiment;

FIG. 9 is a top view of the second embodiment;

FIG. 10 is a cross-sectional side view taken along lines 10—10 of FIG. 9;

FIG. 11 is a cross-sectional end view taken along lines 11—11 of FIG. 9;

FIG. 12 is an exterior end view of the second embodiment; and

DETAILED DESCRIPTION OF A PREFERRED EMBODIMENT

Figure 1:
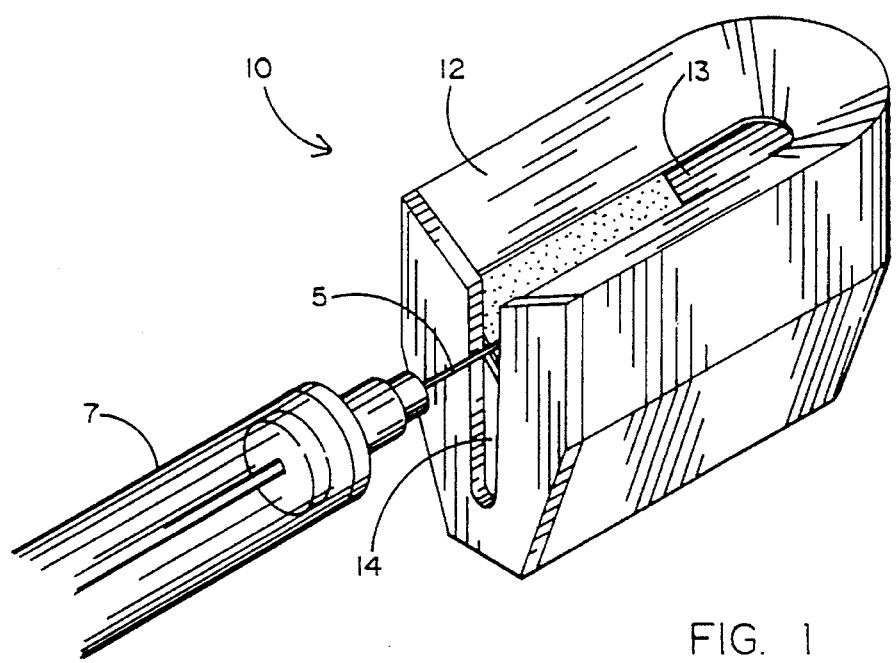
FIG. 1 is an isometric view of a first embodiment of the present invention during insertion therein of a syringe needle.

Referring first to FIG. 1, it will be seen that a first embodiment of a disposable safety guard 10 of the present invention is designed to receive a typical syringe needle 5 from a syringe 7. It will also be seen that the safety guard 10 of the present invention comprises a body member 12, having a slot 13 therein leading to an interior V-shaped chamber 14 in which there is provided a gripper 16. It will be seen further that the interior chamber 14 of the body member 12 has a generally V-shaped cross section, the apex of which is adjacent to the bottom end of the body member 12. As seen further in FIG. 1, because of the V or angled shape of the interior of the body member, when the needle is inserted through the slot 13 and between the respective sides of the gripper 16 and forced in a downward direction towards the apex of the body member, the gripper is progressively compressed between the interior side walls of the body member, thereby causing a tightening of the grip between the gripper 16 and the syringe needle 5.

Figure 2:
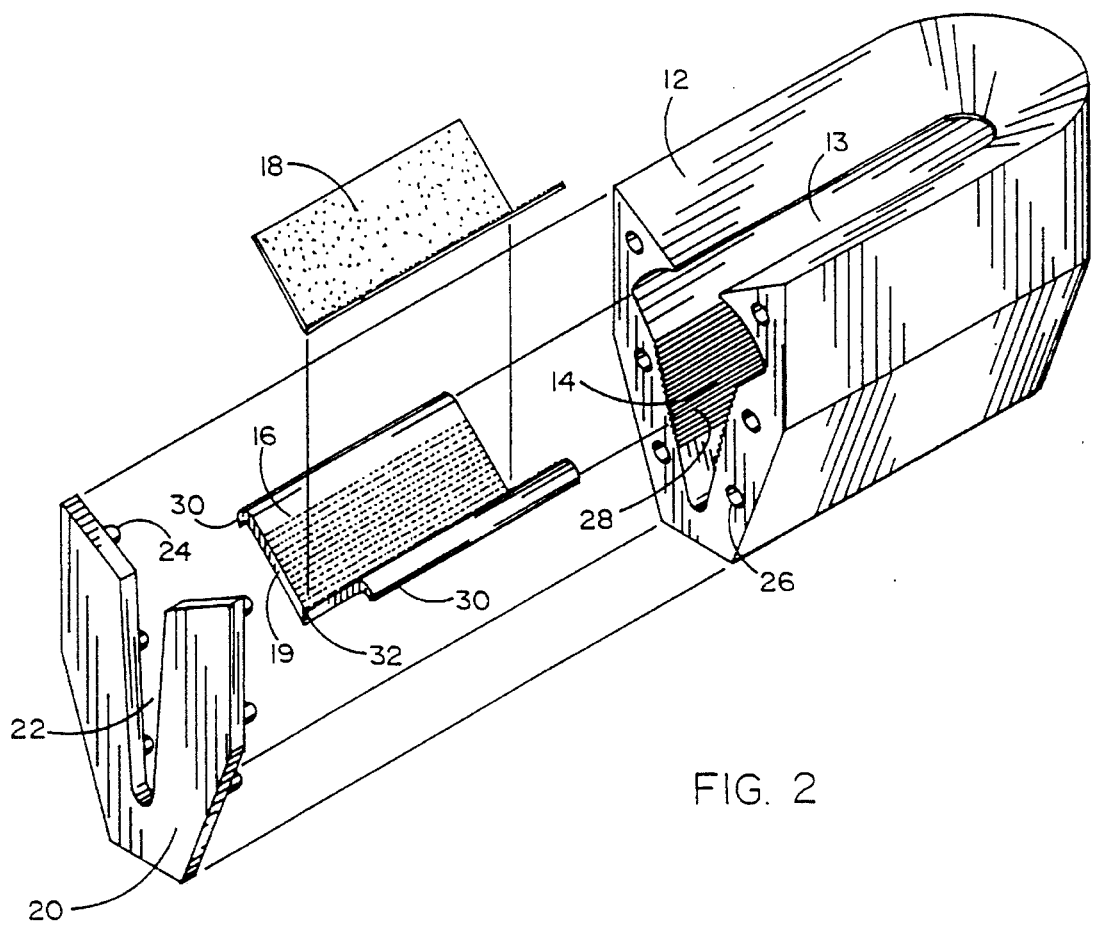
FIG. 2 is an exploded view of the first embodiment of the present invention showing the individual components thereof.

As seen in FIG. 2, gripper 16 is comprised of a generally rectangular planar shaped material having a thinned or living hinge along its midsection, where it may be folded in half. The inside surface of the gripper is provided with a plurality of serrations 19 to increase the gripping affect on the syringe needle. Furthermore, a sandpaper element 18 is inserted along the interior surface and adhesively affixed thereto in order to even further increase the frictional engagement between the gripper and the syringe needle. The upper ends of the folded gripper are provided with respective lips 30 which come to a pointed line edge designed to interface with a plurality of elongated grooves 28 in the interior wall of the body member 12. The interaction of the lips 30 and the grooves 28 produce a ratchet effect which allows the gripper to be inserted further into the V-shaped interior 14 of the body member 12, but which prevents the gripper from moving in the opposite direction towards the upper portion of the body member adjacent slot 13. As seen in FIG. 2, the safety guard 10 also provides a face member 20 designed to cover the front of the body member. More specifically, the face member 20 has a plurality of nipples 24 extending therefrom and the front surface of the body member 12 has a matching plurality of receptacles 26 for receiving the nipples 24. In addition, the face member 20 has an elongated opening 22 which is narrower than the cross section of the V-shaped interior 14 of the body member 12. Opening 22 is designed to permit the syringe needle 5 to be inserted in the V-shaped interior 14 of the body member 12, but is narrow enough to prevent the gripper 16 and sandpaper 18 from being withdrawn from the body member. The gripper 16 and sandpaper 18 are also prevented from sliding away from the face member 20 by means of the interior shape of the walls of the V-shaped interior 14. More specifically, as seen in the top view provided in FIG. 4, the body member 12 has a thin walled portion 15, where the gripper resides and a thick walled portion 17 behind the gripper 16. A shoulder 34 is formed at the transition between the thin walled portion 15 and the thick walled portion 17. Shoulder 34 prevents the rearward movement of the gripper 16 and sandpaper 18.

As seen best in FIGS. 3A and 5, before the syringe needle 5 is inserted into the safety guard 10, the gripper and sandpaper reside at the top most portion of the V-shaped interior 14 with a span between the lips of the gripper 16 being greatest because of their position at the upper most portion of the V-shaped interior. In this position, the gripper may receive the needle 5 of the syringe 7 after it is inserted laterally, parallel to the slot 13, toward the apex or bottom of the body member 12. As the needle 5 hits the thinned hinge 32 of the gripper, it forces the gripper in a downward direction into the narrowing region of the V-shaped interior 14. Consequently, the gripper and sandpaper combination begin to close as the distance between the lips 30 decreases. This closing action occurs in a progressive manner as the needle is forced further down toward the lower most portion of the V-shaped interior until the gripper closes sufficiently to engage the needle in a sandwiching effect or in what may be called a nutcracker effect as shown in FIG. 3B. Of course it will be understood that the extent to which the gripper slides toward the bottom of the V-shaped interior of the body member, depends upon the diameter of the needle 5. However, irrespective of the diameter of the needle, a modest downwardly directed force on the needle toward the hinge 32 of the gripper 16, will create a sufficiently compressive sandwiching force on the needle to prevent it from being extracted from the safety guard.

Figure 7:
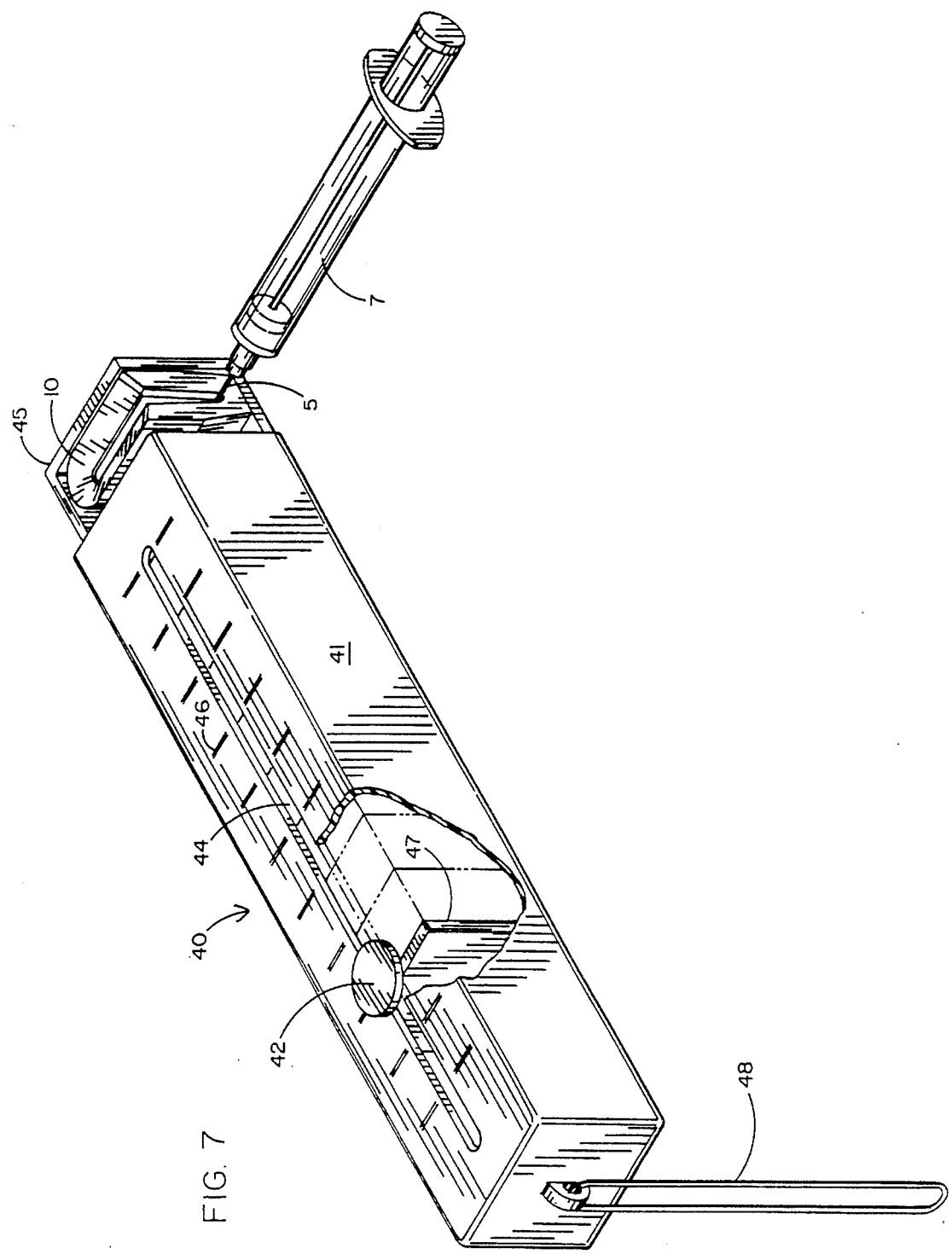
FIG. 7 is a three-dimensional view of a dispenser of the present invention.
Figure 8:
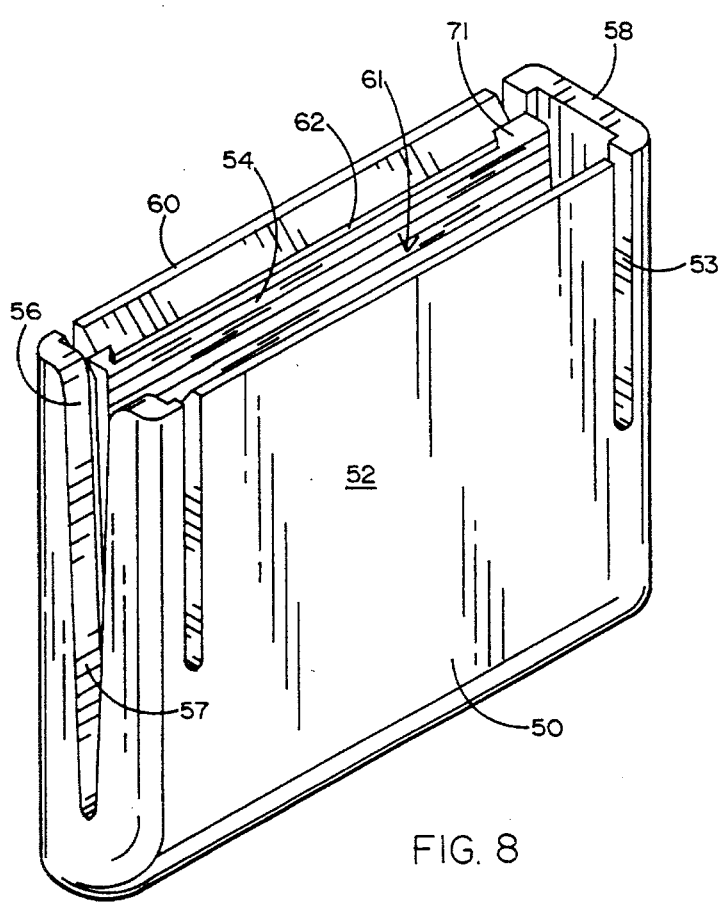
FIG. 8 is a three-dimensional view of a second embodiment of the present invention.

While the safety guard of the present invention is designed to minimize risk of pricking the hands of the user by providing for a translation of the needle into the interior in a direction perpendicular to the axis of the needle, the risk of inadvertent pricking can be even further reduced by using the dispenser 40 shown in FIG. 7. As seen therein, the dispenser 40 comprises an elongated rectangular housing 41 for retaining a plurality of safety guards 10, such as 20–25 such safety guards in a serial array. A push member 42 is provided, which operates for transitional motion within a slot 44 adjacent to which there is a plurality of indicator lines 46. The indicator lines provide an externally accessible indication of the number of safety guards that have been dispensed to date. The safety guards are contained within slotted panels of an internal shelf-like drawer 45. The drawer is pushed by a flap 47, attached directly to the push member 42. A wrist strap 48 may be connected to the dispenser housing at the end of the housing opposite the open end of drawer 45. It will be apparent that the housing is designed to enable use of the guard 10 with only one hand and with a greater distance separating the hand of the user retaining the dispenser and the pointed end of the syringe needle to thereby reduce the risk of inadvertent pricking of the hand or other body parts with a used syringe needle.

A second embodiment of the present invention is disclosed in FIGS. 8 to 16 which shall now be described. Referring to FIGS. 8 to 12, it will be seen that the second embodiment safety guard 50 comprises a housing 52 having a slotted end wall 56, an enclosed end wall 58 and opposed side wall members 60. The slotted end wall 56 provides a tapered slot 57 for receiving a syringe needle placed laterally into a rectangularly-shaped interior chamber 61 formed within the surrounding walls 56, 58 and 60. Along the interior surface of each end wall 60 there are three spaced-apart ratchet ribs 63 each having three vertically spaced ratchet teeth 64, 66 and 68. An elongated flange 62 lies along the top of each wall 60 and projects toward the opposing wall. Each of the ratchet teeth 66 projects into the chamber 61 further than teeth 64 which, in turn, project further into the chamber than teeth 62. A pair of tapered ribs 70 is also provided on the interior surface of each wall 60 adjacent the bottom of the chamber 61 and spaced symmetrically between the ratchet ribs 63.

Figure 13:
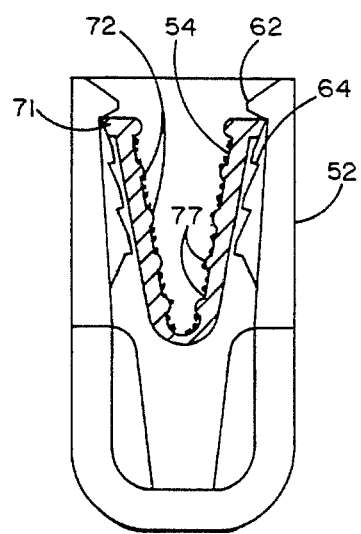
FIGS. 13 to 16 provide sequential illustrations of the interaction of the gripper and interior chamber in the second embodiment.
Figure 14:
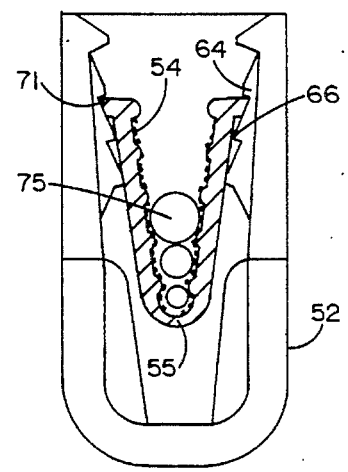
Figures 15, 16:
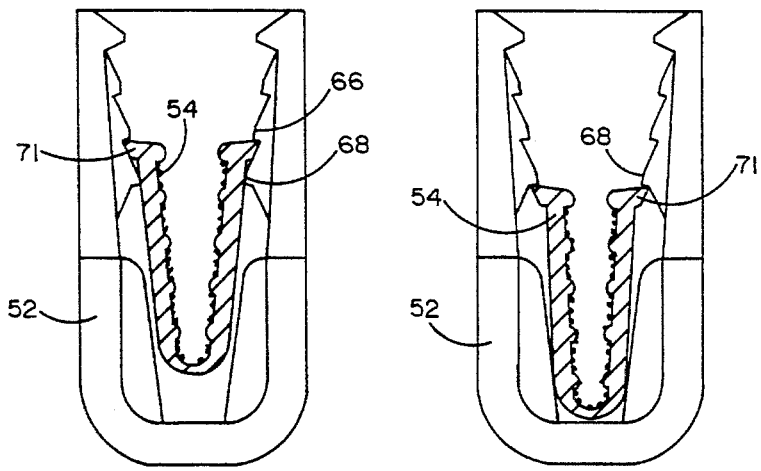

As seen in FIGS. 8 and 13 to 16, safety guard 50 also comprises a gripper 54 which has a pair of externally-facing lips 71 at the upper ends thereof and a plurality of internally-facing ridges 72. FIG. 13 illustrates the guard 50 configured for receiving a syringe needle before the needle is inserted into the guard. In this configuration the lips 71 of the gripper 54 are secured below the flanges 62 preventing the upward vertical movement of the gripper. As a needle 75 (three sizes are shown in FIG. 14) applies downward force against the gripper, the lips 71 are progressively ratcheted down as shown sequentially in FIGS. 14, 15 and 16 while hinge 55 bends further increasing the gripping relation between the gripper ridges 72 and the needle shaft. The tapered ribs 70 provide added security against inadvertent expansion of the gripper. Slots 53, which separate the walls 60 from ends 56 and 58 respectively, permit a limited expansion of the chamber 61 to permit tool withdrawal during injection molding. The gripper 54 is preferrably made of homopolypropylene which, while at high temperature, may be sprinkled with fine particles 77 of aluminum oxide which are retained in the soft surface of the plastic and increase the frictional engagement between the gripper and a needle. Because of the relative position of the lips 71, which are the compression locations for teeth 64, 66 and 68 and the needle 75, there is a leverage effect much like a nut cracker to firmly grasp and retain the needle within the gripper.

It will now be understood that what has been disclosed herein comprises a novel disposable safety guard for syringe needles which satisfies all of the aforementioned objects of the invention and which overcomes the aforementioned disadvantages of the prior art. It will now be apparent to those having skill in the art to which the present invention pertains, that various modifications and additions may be made to the invention with the benefit of the applicant's teaching herein. By way of example, the precise shape, dimensions and materials disclosed herein by way of description of an exemplary embodiment of the invention, may be readily altered while still achieving the advantageous results provided hereby. Accordingly, all such modifications and additions are deemed to be within the scope of the invention, which is to be limited only by the claims attached hereto and their equivalents.

I claim:

1. A device for laterally receiving and enclosing the end of a syringe needle; the device comprising:

a body member having an elongated slot and an interior chamber, said elongated slot leading into said interior chamber;

a gripping member positioned with said chamber for receiving said needle, said gripping member having a pair of planar portions joined by a hinge, said planar portions resting against respective opposing interior walls within said chamber;

said planar portions having respective lips, one such lip on each of said planar portions;

said interior walls having a plurality of ratchet teeth for receiving said lips whereby said gripping member can translate in only one direction thereby drawing said planar members toward one another for compressive gripping said needle therebetween;

further comprising a high friction gripping material on said planar portions for frictionally engaging said needle;

said gripping material comprises aluminum oxide particles.

2. A device for attachment to the sharp end of a needle; the device comprising:

a hinged gripper for receiving said needle end;

a housing containing said gripper within an elongated chamber, the chamber having an elongated opening for receiving said needle; and means for closing said gripper around said hinge on said needle end as said needle is translated in a direction substantially perpendicular to said needle from said opening within said chamber;

further comprising a rough surface material on said gripper for retaining said needle;

wherein said rough surface material is aluminum oxide.

3. A hypodermic needle safety system comprising a plurality of guards for attachment to syringe needles to prevent inadvertent pricking after use of a syringe prior to disposal of the syringe;

each said guard having a hinged gripping device for laterally receiving one said needle in compressive surrounding engagement therewith; and a dispenser containing said plurality of guards in a serial array and having means for providing access to one such guard at a time;

wherein each said guard comprises a body member having an elongated chamber for receiving said gripping device and for closing said gripping device around said needle upon translation of said gripping device within said chamber by the force of said needle;

wherein each such guard further comprises ratchet teeth for permitting translation of said gripping device in only one direction toward the interior of said chamber;

wherein each said gripping device comprises a plastic material having embedded particles of aluminum oxide.

4. The system recited in claim 3 wherein said plastic material is homopolypropylene.

* * * * *